United States Patent
Vaartstra

(10) Patent No.: US 9,683,937 B2
(45) Date of Patent: Jun. 20, 2017

(54) IMAGING DEVICES FOR MOLECULE DETECTION

(71) Applicant: Semiconductor Components Industries, LLC, Phoenix, AZ (US)

(72) Inventor: Brian Vaartstra, Nampa, ID (US)

(73) Assignee: SEMICONDUCTOR COMPONENTS INDUSTRIES, LLC, Phoenix, AZ (US)

( * ) Notice: Subject to any disclaimer, the term of this patent is extended or adjusted under 35 U.S.C. 154(b) by 98 days.

(21) Appl. No.: 14/290,615

(22) Filed: May 29, 2014

(65) Prior Publication Data

US 2015/0056097 A1  Feb. 26, 2015

Related U.S. Application Data

(60) Provisional application No. 61/869,305, filed on Aug. 23, 2013.

(51) Int. Cl.
*G01N 21/64* (2006.01)

(52) U.S. Cl.
CPC .................. *G01N 21/6454* (2013.01)

(58) Field of Classification Search
CPC ...... G01N 21/6454; C12Q 1/6869; G03F 7/16
See application file for complete search history.

(56) References Cited

U.S. PATENT DOCUMENTS

| | | | | |
|---|---|---|---|---|
| 5,096,807 A * | 3/1992 | Leaback | ............. | G01N 33/535 422/50 |
| 5,143,854 A * | 9/1992 | Pirrung | ............. | G01N 21/6428 435/7.92 |
| 5,854,684 A * | 12/1998 | Stabile | ............. | G01N 21/253 356/417 |
| 6,458,547 B1 * | 10/2002 | Bryan | ............. | G01N 21/253 356/215 |
| 6,800,438 B2 | 10/2004 | Noolandi et al. | | |

(Continued)

OTHER PUBLICATIONS

"Corning Assay Surfaces: DNA-BIND (N-oxysuccinimide) Modified Surface" [online] retrieved on May 29, 2014 <URL: http://www.corning.com/lifesciences/us_canada/en/technical_resources/surfaces/assay/dnabind_modified.aspx>.

(Continued)

*Primary Examiner* — Lore Jarrett
(74) *Attorney, Agent, or Firm* — Treyz Law Group, P.C.; Joseph F. Guihan

(57) ABSTRACT

An imager may include an array of pixels formed on a substrate. A chemisorption layer such as a planar chemisorption layer may be deposited over the array of pixels. The chemisorption layer may include active sites that bond with anchoring molecules. The anchoring molecules may be bonded to the planar chemisorption layer in only localized regions each covering a respective pixel of the array of pixels. The image sensor may include a photoresist layer that covers the chemisorption layer. Openings in the photoresist layer may define the boundaries of the localized regions. The anchoring molecules may be bonded only with the chemisorption layer without bonding to the photoresist layer. The anchoring molecules may serve to bond with analyte molecules. By forming the anchoring molecules within only localized regions centered over respective pixels, spatial resolution of the imager when imaging the analyte molecules may be improved.

14 Claims, 6 Drawing Sheets

(56) References Cited

U.S. PATENT DOCUMENTS

| | | | |
|---|---|---|---|
| 6,897,026 B2* | 5/2005 | Lamont | G01N 21/253 |
| | | | 422/68.1 |
| 8,361,784 B2* | 1/2013 | Oshida | G01N 21/6428 |
| | | | 250/461.2 |
| 8,502,867 B2 | 8/2013 | Park | |
| 8,698,481 B2 | 4/2014 | Lieber et al. | |
| 2003/0148401 A1* | 8/2003 | Agrawal | B01J 19/0046 |
| | | | 506/9 |
| 2003/0235924 A1* | 12/2003 | Adams | B01L 3/502715 |
| | | | 436/172 |
| 2010/0108865 A1* | 5/2010 | Cho | G01N 21/6452 |
| | | | 250/216 |

OTHER PUBLICATIONS

"Corning Assay Surfaces: Sulfhydryl-BIND (Maleimide) Modified Surface" [online] retrieved on May 29, 2014 <URL: http://www.corning.com/lifesciences/us_canada/en/technical_resources/surfaces/assay/sulfhydrylbind_modified.aspx>.

"Corning Assay Surfaces: Carbo-BIND (Hydrazide) Modified Surface" [online] retrieved on May 29, 2014 <URL: http://www.corning.com/lifesciences/us_canada/en/technical_resources/surfaces/assay/carbobind_modified.aspx>.

* cited by examiner

IMAGING DEVICES FOR MOLECULE DETECTION

This application claims the benefit of provisional patent application No. 61/869,305, filed Aug. 23, 2013, which is hereby incorporated by reference herein in its entirety.

BACKGROUND

This relates generally to imaging systems, and more particularly to imaging systems for detection of chemical molecules.

Modern electronic devices such as cellular telephones, cameras, and computers often use digital image sensors. Imagers (i.e., image sensors) may be formed from a two-dimensional array of image sensing pixels. Each pixel receives incident photons (light) and converts the photons into electrical signals. Image sensors are sometimes designed to provide images to electronic devices using a Joint Photographic Experts Group (JPEG) format.

Imager sensors are sometimes used in microfluidic devices to image molecules. A molecule that is to be imaged may sometimes be referred to herein as an analyte or an analyte molecule. In such scenarios, an image sensor has an active surface that is covered with a layer of a chemical anchoring agent which bonds with molecules such as deoxyribonucleic acid (DNA). A fluorescent emitter is selectively attached to the molecules and light emitted by the fluorescent molecules is captured and converted into image data by the image sensors. However, the molecules bond randomly over the chemical anchoring agent layer and therefore there is the potential for cross-talk between image pixels. For example, a DNA strand may bond to the active surface of the image sensor in a region between multiple pixels such that light emitted by a fluorescent molecule coupled to the DNA strand is absorbed by each of the pixels.

To help reduce the effects of cross-talk, the active surface of the image sensor is sometimes etched to form wells prior to depositing the chemical anchoring agent layer. Subsequently, a mechanical polishing step is performed to remove the chemical anchoring agent in regions outside of the wells of the active surface. However, mechanical polishing to remove chemical anchoring agents can be unreliable and subject to substantial manufacturing variations. It would therefore be desirable to provide imagers with improved spatial resolution.

DETAILED DESCRIPTION

Figure 1:
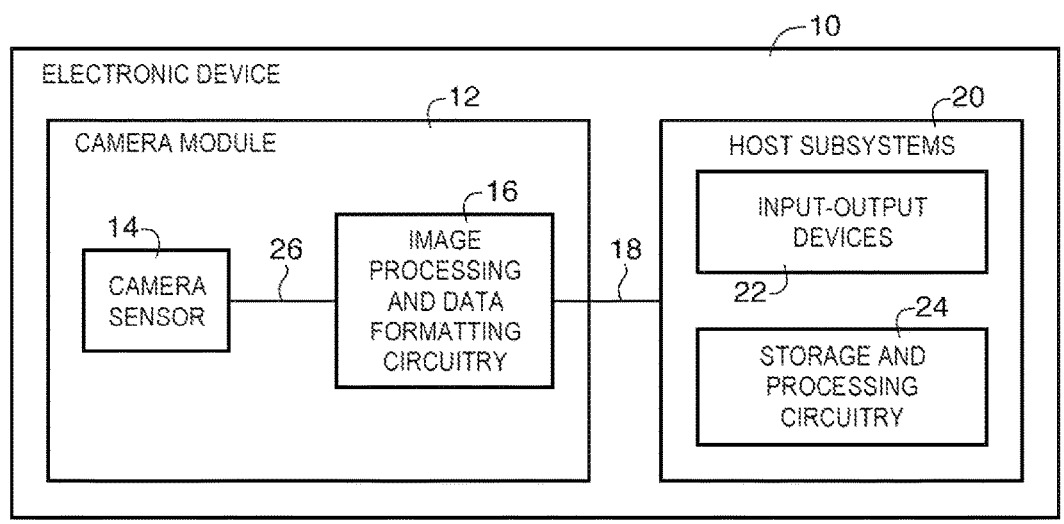
FIG. 1 is an illustrative schematic diagram of an electronic device with a camera sensor with improved spatial resolution for imaging molecules in accordance with an embodiment of the present invention.

Embodiments of the present invention relate to image sensors for microfluidic devices. An electronic device with a digital camera module is shown in FIG. 1. Electronic device 10 may be a microfluidic device, digital camera, a computer, a cellular telephone, a medical device, or other electronic device. Camera module 12 may include image sensor 14 and one or more lenses. During operation, the lenses focus light onto image sensor 14. Image sensor 14 includes photosensitive elements (e.g., pixels) that convert the light into digital data. Image sensors may have any number of pixels (e.g., hundreds, thousands, millions, or more). A typical image sensor may, for example, have millions of pixels (e.g., megapixels). As examples, image sensor 14 may include bias circuitry (e.g., source follower load circuits), sample and hold circuitry, correlated double sampling (CDS) circuitry, amplifier circuitry, analog-to-digital (ADC) converter circuitry, data output circuitry, memory (e.g., buffer circuitry), address circuitry, etc.

Still and video image data from camera sensor 14 may be provided to image processing and data formatting circuitry 16 via path 26. Image processing and data formatting circuitry 16 may be used to perform image processing functions such as molecule imaging (e.g., for molecule sequencing such as DNA sequencing), three-dimensional depth sensing, data formatting, adjusting white balance and exposure, implementing video image stabilization, face detection, etc. Image processing and data formatting circuitry 16 may also be used to compress raw camera image files if desired (e.g., to Joint Photographic Experts Group or JPEG format). In a typical arrangement, which is sometimes referred to as a system on chip (SOC) arrangement, camera sensor 14 and image processing and data formatting circuitry 16 are implemented on a common integrated circuit. The use of a single integrated circuit to implement camera sensor 14 and image processing and data formatting circuitry 16 can help to reduce costs.

Camera module 12 may convey acquired image data to host subsystems 20 over path 18 (e.g., image processing and data formatting circuitry 16 may convey image data to subsystems 20). Electronic device 10 typically provides a user with numerous high-level functions. In a computer or advanced cellular telephone, for example, a user may be provided with the ability to run user applications. To implement these functions, host subsystem 20 of electronic device 10 may include storage and processing circuitry 24 and input-output devices 22 such as keypads, input-output ports, joysticks, and displays. Storage and processing circuitry 24 may include volatile and nonvolatile memory (e.g., random-access memory, flash memory, hard drives, solid state drives, etc.). Storage and processing circuitry 24 may also include microprocessors, microcontrollers, digital signal processors, application specific integrated circuits, or other processing circuits.

Figure 2:
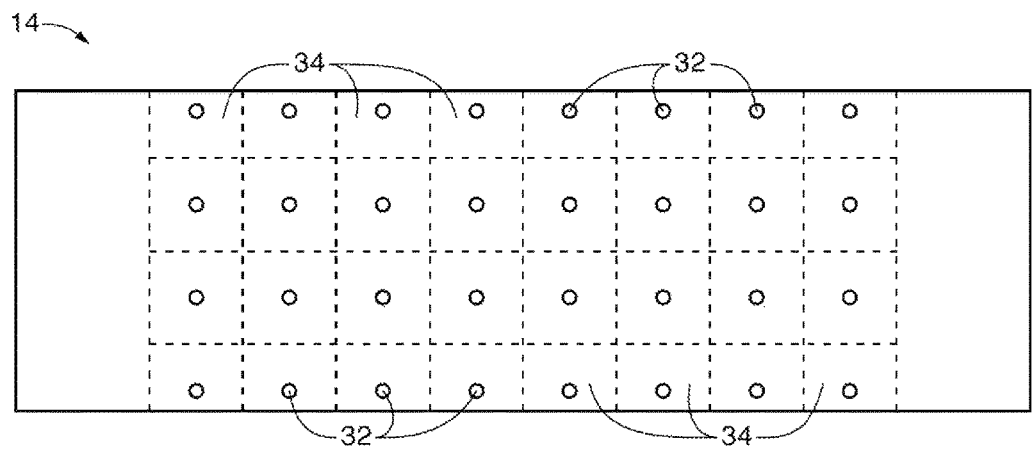
FIG. 2 is an illustrative top view of an image sensor having improved spatial resolution for imaging molecules in accordance with an embodiment of the present invention.

Image sensors may be provided with improved spatial resolution of fluorescent molecules. An active surface of the image sensor may be selectively covered with chemical anchoring agent molecules such that the anchoring molecules are localized over the pixels of an image sensor pixel array. FIG. 2 is an illustrative active surface view of an image sensor showing how the image sensor may be provided with improved spatial resolution.

As shown in FIG. 2, an image sensor 14 may include an array of pixels 34 arranged in rows and columns. Pixels 34 include photosensitive regions that capture incident light and convert the captured light into electrical signals. Anchoring agents may be deposited within localized regions 32 of pixels 34. In the example of FIG. 2, localized regions 32 are circular regions. This is merely illustrative. If desired, regions 32 may be any desired shape (e.g., square, rectangular, etc.) that covers only a portion of respective pixels 34. The anchoring agents serve to bond with analytes (i.e., molecules of interest to be imaged by image sensor 14). The analytes may be subsequently tagged with fluorescent molecules. The fluorescent molecules may, for example, be attached selectively to portions of the analytes to identify the selected portions. In response to a stimulating energy source such as light, the fluorescent molecules may emit light (e.g., at a different wavelength than the stimulating energy source). The light emitted by the fluorescent molecules may be captured and converted to electrical signals by the pixels to produce image data for the analytes.

By selectively attaching the anchoring agents over centralized regions of each of the imaging pixels, spatial resolution of the image sensors may be improved, because light emitted by fluorescent molecules coupled to the anchoring agents are spatially separated between image pixels. Cross-talk between pixels from light emitted by the fluorescent molecules may be reduced, because the anchoring agents are centered over each of the imaging pixels and no fluorescent molecules are attached over regions between imaging pixels.

Figure 3:
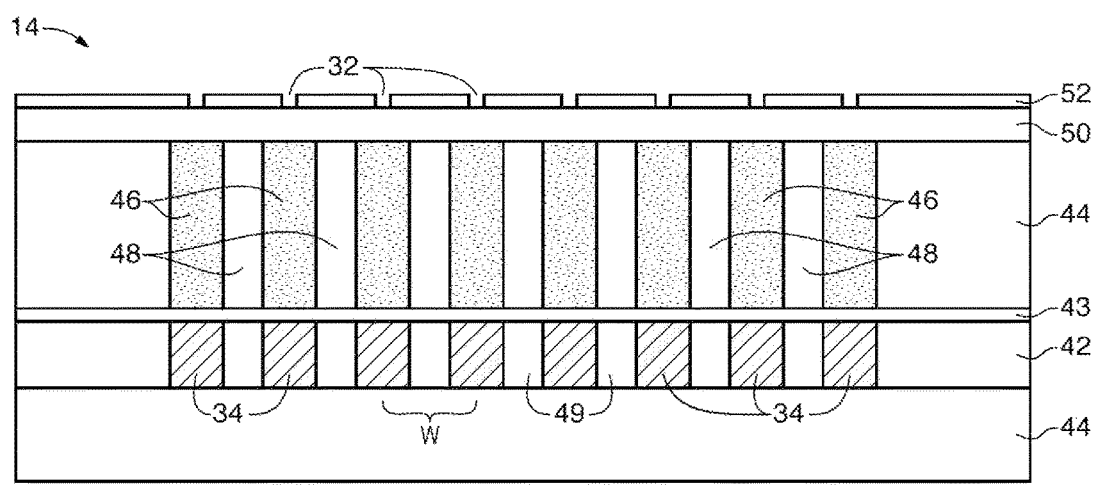
FIG. 3 is an illustrative cross-sectional view of an image sensor in which patterned photoresist provides improved spatial resolution for imaging molecules in accordance with an embodiment of the present invention.

FIG. 3 is an illustrative cross-section of an image sensor 14 that may be provided with improved spatial resolution capabilities. As shown in FIG. 3, image sensor 14 includes pixels 34 formed in substrate 42. Substrate 42 may, for example, be a semiconductor substrate such as silicon. Pixels 34 may be formed by doping regions of the substrate to create photosensitive regions, transistors, or other circuitry. Layer 44 may include one or more metal interconnect layers including metal paths for interconnecting pixels 34.

In the example of FIG. 3, image sensor 14 is configured as back-side illumination (BSI) sensor, because incoming light is received at substrate 42 instead of through layer 44. This example is merely illustrative. If, desired, image sensor 14 may be configured as a front-side illumination (FSI) sensor in which light is received by pixels 34 through layer 44 (e.g., through metal interconnect layers).

Substrate 42 may be covered by a passivation layer 43 that serves as a barrier to help protect pixels 34 in substrate 42. For example, barrier layer 43 may be formed from silicon oxide, silicon nitride, or other protective materials. Barrier layer 43 may be interposed between substrate 42 and color filter layer 44.

Color filter layer 44 may cover substrate 42 and includes color filter elements 46. For example, color filter layer 44 may be an oxide layer. Color filter elements 46 may pass light that is within a predetermined range of wavelengths to underlying pixels 34 (e.g., each pixel 34 may have a corresponding color filter element 46). Color filter elements 46 may block or otherwise prevent passage of light having wavelengths outside of the predetermined range. As examples, color filter elements 46 may pass only red light, green light, or blue light. If desired, color filter elements may pass light having non-visible wavelengths. For example, color filter elements may pass ultraviolet light.

Color filter elements 46 may be separated by regions 48 of color filter layer 44. Regions 48 may be formed from oxide or other materials having a different index of refraction from color filter elements 46 such that color filter elements 46 serve as waveguides for passing light to pixels 34. Pixels 34 may be separated by distance W and inter-pixel regions 49 (e.g., regions of substrate 42 that are not photosensitive). Distance W may, for example, be 1.1 um.

Chemisorption layer 50 may be deposited to cover color filter layer 44 (e.g., as a planar layer). Chemisorption layer 50 is formed from material that chemically reacts with anchor molecules to form bonds between layer 50 and the anchor molecules. For example, chemisorption layer 50 may be formed from a polymer layer having active sites for bonding with anchor molecules. The active sites may be distributed throughout the surface of layer 50 and may be formed from hydroxyl groups that terminate the polymers of the layer. An example polymer with hydroxyl groups includes phenolic resins and Novolac. Alternatively, the active sites may be composed of other reactive pendant groups of the polymer including benzyl halides, alkyl halides, alkoxide, olefin, dienyl, thiol, amino, amido, and ester groups. Use of a polymer layer 50 may help to ensure chemical stability during highly alkaline conditions that may be used in subsequent processing steps (e.g., during analyte sequencing steps). If desired, other materials may be used to form chemisorption layer 50. For example, chemisorption layer 50 may be formed from surface oxides such as silicon oxide or metal oxides having surface hydroxyl groups or other active sites for bonding with anchoring agents.

Per-pixel localized regions 32 may be formed using photolithographic patterning. In the example of FIG. 3, photoresist layer 52 may be deposited (e.g., initially as a uniform, continuous layer) and subsequently patterned using photolithography to form openings in layer 52 for regions 32. Photoresist layer 52 may be formed from a polymer that is less active toward chemisorption by the anchor molecules than chemisorption layer 50 (e.g., photoresist layer 52 has minimal or no active sites that bond with the anchor molecules).

Figure 4:
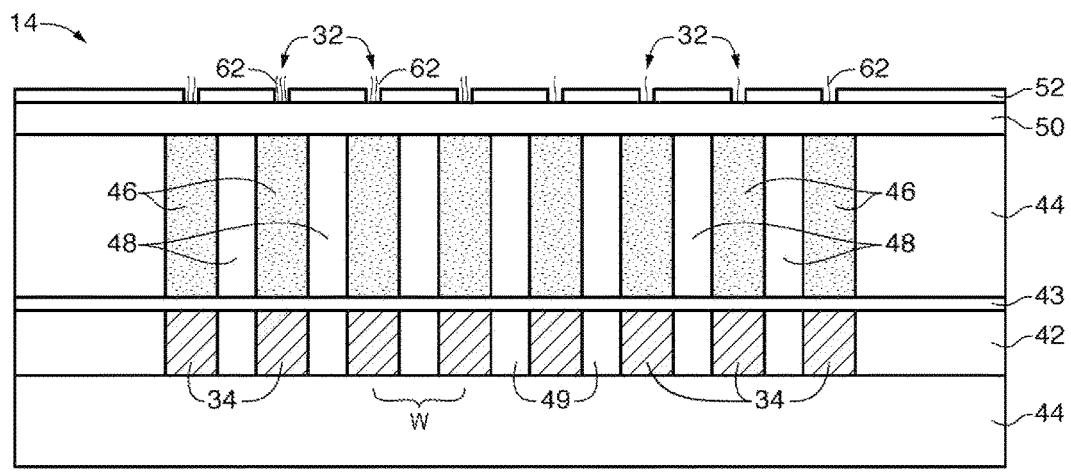
FIG. 4 is an illustrative cross-sectional view of an image sensor showing how anchoring molecules may be deposited only in localized regions that cover respective pixels in accordance with an embodiment of the present invention.

As shown in FIG. 4, anchor molecules 62 may be deposited in regions 32 (e.g., openings of photoresist layer 52). Anchor molecules 62 may be deposited using gas or solution-based deposition techniques. For example, anchor molecules 62 may be deposited using a vapor deposition process in which anchor molecules 62 are passed as a gas over the surface of layer 52. As another example, anchor molecules 62 may be included in a solution that is used to coat the wafer using spin-on or tank-dip processes.

Anchor molecules 62 tend to chemically bond with chemisorption layer 50 while remaining detached from layer 52 (e.g., anchor molecules 62 bond with layer 50 without bonding with layer 52). For example, anchor molecules 62 may include an exposed silicon chloride compound that reacts with hydroxyl active sites on layer 50 to produce a silicon oxide (Si—O) bond between anchor molecules 62 and chemisorption layer 50. Other anchor-molecule functional groups can bond to the surface by similar condensation reactions, for example, hydroxyl, silylamino, amino, thiolato, alkenyl, dienyl, alkoxy, ester, hydrazido groups and the like. Anchor molecules may have more than one point of attachment to layer 50. An example is $(CH_3O)_3SiCH_2CH_2CH_2NH_2$. Anchor molecules will necessarily be at least bi-functional. In other words, the anchor molecules contain at least one reactive group that binds to surface 50 and another group (preferably separated from the first group by at least two non-reactive groups as shown in the example above). Anchor molecules 62 may therefore localize at regions 32 of layer 50 that are centered over underlying pixels 34. Localization of anchor molecules 62 over pixels 34 may help to improve spatial resolution and reduce cross-talk between pixels.

Figure 5:
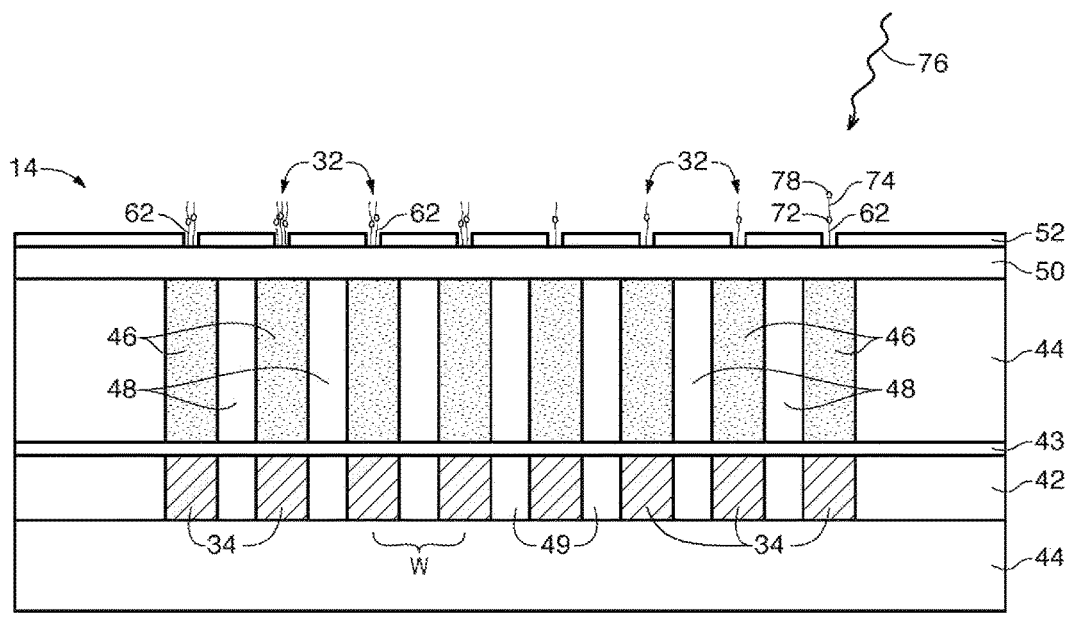
FIG. 5 is an illustrative cross-sectional view of an image sensor showing how anchoring molecules in localized regions may bond with analyte molecules for imaging in accordance with an embodiment of the present invention.

As shown in FIG. 5, anchor molecules 62 may serve as bonding agents for analytes 74 (i.e., molecules of interest that are to be imaged). For example, anchor molecules 62 may include exposed bonding sites 72 that tend to chemically bond with analytes 74. For example, in the scenario in which analytes 74 are DNA molecules, bonding sites 72 may include a compound formed from nitrogen and hydrogen (e.g., $NH_2$) that bonds with analytes 74. Other examples of anchor-molecule functional groups that specifically bond to biomolecules include N-oxysuccinimide esters, maleimides, and hydrazides. Chemical bonding of the anchor molecules to the active surface 50, or subsequent bonding of the analyte molecules may optionally be assisted by ultraviolet light and/or catalysts added to the reaction mixture. In some cases it may be desirable to chemically bond a second bi-functional layer to the primary anchor molecule layer. Such layer may serve to terminate the surface with reactive groups that target specific functional groups of the analyte.

During subsequent imaging operations, a source of stimulation 76 such as light may be used to stimulate fluorescence associated with analytes 74. If desired, fluorescent emitters 78 may be deposited that bond with selected analytes 74 (e.g., fluorescent emitters 78 may bond with each strand of analytes 74 depending on the chemical makeup of that particular strand). In response to receiving stimulation 76, fluorescent emitters 78 may emit light at a predetermined wavelength or range of wavelengths based on the properties of emitters 78. The emission wavelength may be different from the wavelengths of stimulating light 76. Layer 52 may be formed from a polymer that tends not to react with stimulating light 76 (e.g., layer 52 has low or minimum autofluorescence). Emitted light may be passed through layer 50 and color filter elements 46 to pixels 34 for producing electrical image signals.

In some scenarios, fluorescent emitters 78 may be selectively removed and attached to analytes 74 (e.g., via grafting and/or deposition processes). For example, sequencing processes such as DNA sequencing or sequencing of other molecules may perform a series of steps under alkaline conditions (e.g., having a pH level of 8-12). In this scenario, it may be desirable for photoresist layer 52 to be formed from a polymer that is stable during alkaline conditions. A polymeric layer 52 may help to protect underlying chemisorption layer 50 (e.g., when layer 50 is formed from a material that is less stable during alkaline conditions such as silicon oxide).

Figure 6:
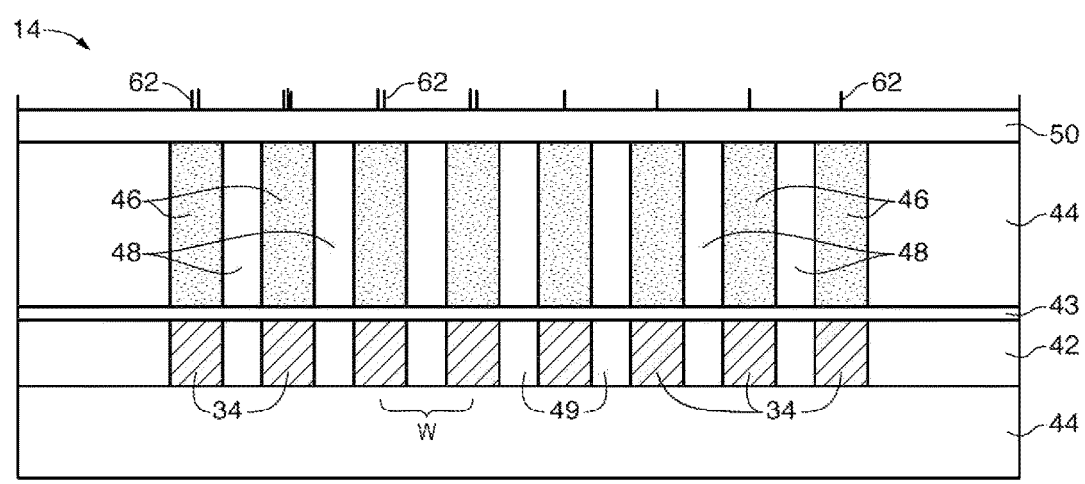
FIG. 6 is an illustrative cross-sectional view of an image sensor showing how photoresist may be removed while maintaining improved spatial resolution in accordance with an embodiment of the present invention.

If desired, photoresist layer 52 may be removed subsequent to depositing anchoring agents 62 as shown in FIG. 6. In the example of FIG. 6, chemisorption layer 50 serves as a top surface of image sensor 14. In this scenario, it may be desirable to form chemisorption layer 50 from a material that is stable during alkaline conditions while also providing active sites for bonding with anchoring agents 62 and minimum autofluorescence. For example, chemisorption layer 50 may be a polymeric layer that has active bonding sites and does not emit light in response to stimulation 76 of FIG. 5. The removal of photoresist layer 52 may be preferred, for example, if the anchoring agents exhibit some bonding, perhaps even weak bonding (e.g. physisorption) to the photoresist layer.

Figure 7:
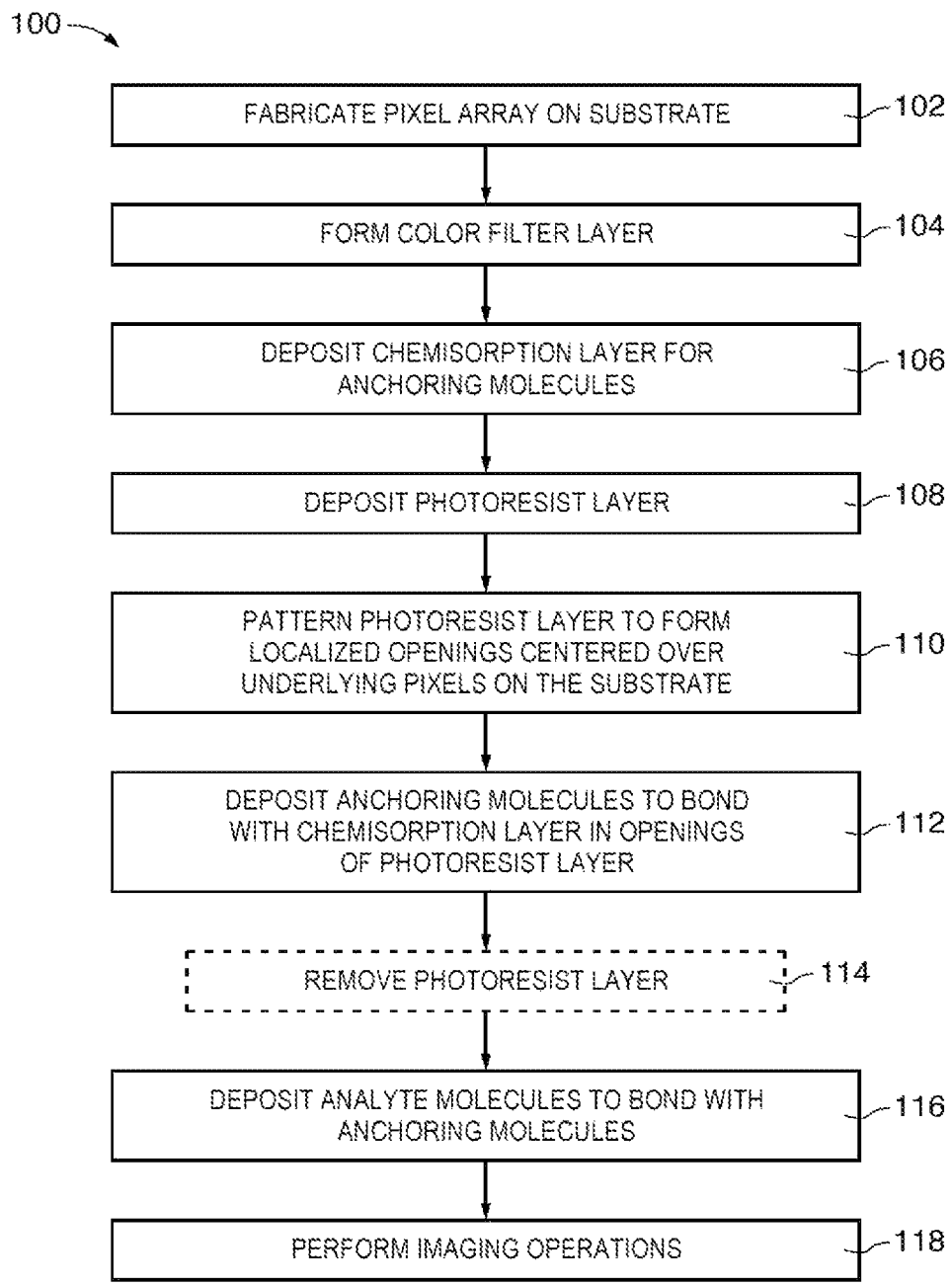
FIG. 7 is a flow chart of illustrative steps that may be performed in fabricating an image sensor with improved spatial resolution for imaging molecules in accordance with an embodiment of the present invention.

FIG. 7 is a flow chart of illustrative steps that may be performed in forming an imager with improved spatial resolution of analyte molecules.

During step 102, semiconductor fabrication tools may be used to fabricate a pixel array on a substrate (e.g., an array of pixels 34 on substrate 42 as shown in FIG. 3). The fabrication tools may be used to fabricate circuitry on substrate 42 such as readout circuitry, amplifier circuitry, storage circuitry, or other circuitry for the imager.

During step 104, a color filter layer may be formed over the imager substrate. For example, color filter layer 44 and color filter elements 46 may be formed over pixels 34 as shown in FIG. 3.

During step 106, deposition tools may be used in depositing a chemisorption layer (e.g., layer 50 of FIG. 3). The chemisorption layer may include active sites for bonding with anchoring molecules. As an example, vapor deposition tools, spin-on tools, or tank-dipping tools may be used in depositing the chemisorption layer.

During step 108, deposition tools may be used in depositing a photoresist layer (e.g., photoresist layer 52 of FIG. 3). During subsequent step 110, photolithography tools may be used to pattern the photoresist layer to form localized openings that are centered over underlying pixels on the imager substrate.

During step 112, deposition tools may be used to deposit anchoring molecules to bond with the chemisorption layer in the localized openings of the photoresist layer. The anchoring molecules may therefore be centered over the pixels of the imager, which helps to improve spatial resolution and reduce cross-talk between pixels.

If desired, during optional step 114, the patterned photoresist layer may be removed (e.g., using etching or stripping tools) to expose the underlying chemisorption layer. In this scenario, the chemisorption layer may be formed from a material that is resistant to alkaline conditions. In scenarios such as when the photoresist layer is maintained, the photoresist layer may be formed from a material that is resistant to alkaline conditions.

During step 116, analyte molecules (e.g., DNA molecules or other molecules for imaging) may be deposited to bond with the anchoring molecules. The analyte molecules tend to bond with only the anchoring molecules and are therefore localized and centered over underlying pixels. During subsequent step 118, imaging operations may be performed on the analyte molecules. For example, sequencing steps may be performed to selectively attach fluorescent molecules to the analyte molecules, provide stimulating light at a first wavelength, and capture fluorescent light from the fluorescent molecules at a second, different wavelength using the pixels.

Figure 8:
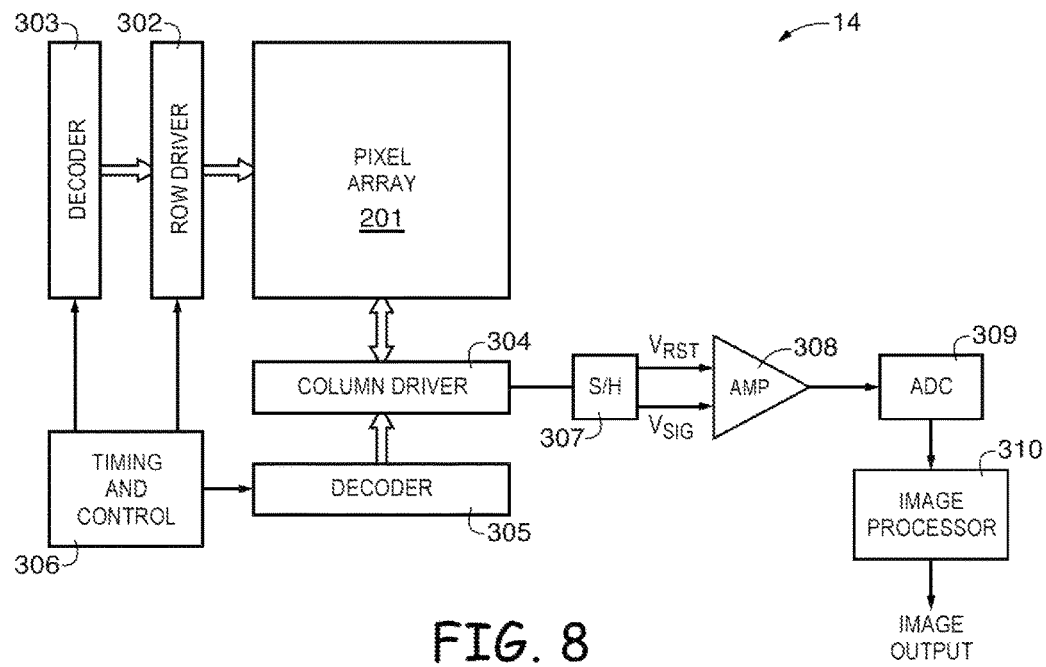
FIG. 8 is a block diagram of an imager employing an image sensor with improved spatial resolution in accordance with an embodiment of the present invention.

FIG. 8 illustrates a simplified block diagram of an imager 14, for example a CMOS imager, employing a pixel array 301 (e.g., including pixels 34 formed in a substrate 42 as shown in FIG. 3) and other circuitry that may be formed on an imaging substrate. Pixel array 301 includes a plurality of pixels arranged in a predetermined number of columns and rows. The row lines are selectively activated by the row driver 302 in response to row address decoder 303 and the column select lines are selectively activated by the column driver 304 in response to column address decoder 305. Thus, a row and column address is provided for each pixel.

Imager 14 is operated by a timing and control circuit 306, which controls decoders 303 and 305 for selecting the appropriate row and column lines for pixel readout, and row and column driver circuitry 302, 304, which apply driving voltages to the drive transistors of the selected row and column lines. The pixel signals, which typically include a pixel reset signal Vrst and a pixel image signal Vsig for each pixel (or each photosensitive region of each pixel) are sampled by sample and hold circuitry 307 associated with the column driver 304. A differential signal Vrst-Vsig is produced for each pixel (or each photosensitive area of each pixel), which is amplified by an amplifier 308 and digitized by analog-to-digital converter 309. The analog to digital converter 309 converts the analog pixel signals to digital signals, which are fed to an image processor 310 which forms a digital image. Image processor 310 may, for example, be provided as part of image processing and data formatting circuitry 16 of FIG. 1.

Figure 9:
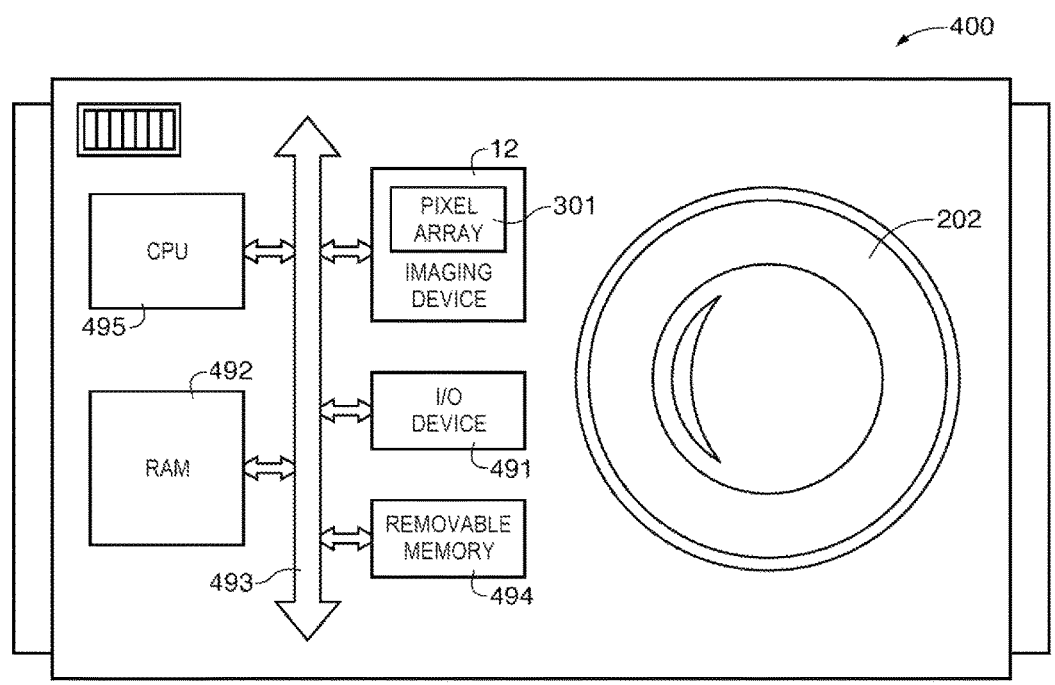
FIG. 9 is a block diagram of a processor system employing the imager of FIG. 8 in accordance with an embodiment of the present invention.

FIG. 9 is a simplified diagram of an illustrative processor system 400, such as a digital camera, which includes an imaging device 12 (e.g., the camera module of FIG. 1) employing an imager with improved spatial resolution for imaging molecules as described above. The processor system 400 is exemplary of a system having digital circuits that could include imaging device 12. Without being limiting, such a system could include a molecule imaging system (e.g., for sequencing DNA or other molecules), computer system, still or video camera system, scanner, machine vision system, vehicle navigation system, video phone, surveillance system, auto focus system, star tracker system, motion detection system, image stabilization system, and other systems employing an imaging device.

Processor system 400, for example a molecule imaging system, generally includes a lens 202 for focusing an image on pixel array 301, central processing unit (CPU) 495, such as a microprocessor which controls camera and one or more image flow functions, which communicates with one or more input/output (I/O) devices 491 over a bus 493. Imaging device 12 also communicates with CPU 495 over bus 493. System 400 also includes random access memory (RAM) 492 and can optionally include removable memory 494, such as flash memory, which also communicates with CPU 495 over the bus 493. Imaging device 12 may be combined with the CPU, with or without memory storage on a single integrated circuit or on a different chip. Although bus 493 is illustrated as a single bus, it may be one or more busses, bridges or other communication paths used to interconnect system components of system 400.

Various embodiments have been described illustrating imagers with improved spatial resolution. An imager may include an array of pixels formed on a substrate. A chemisorption layer such as a planar chemisorption layer may be deposited over the array of pixels. The chemisorption layer may include active sites that bond with anchoring molecules. The anchoring molecules may be bonded to the planar chemisorption layer in only localized regions each covering a respective pixel of the array of pixels. Regions of the chemisorption layer outside of the localized regions are bonded with minimum or no anchoring molecules. The image sensor may include a photoresist layer that covers the chemisorption layer. Openings in the photoresist layer may define the boundaries of the localized regions. The anchoring molecules may be bonded only with the chemisorption layer without bonding to the photoresist layer. The photoresist layer may be formed from a material that is chemically stable during alkaline conditions such as a polymer. If desired, the photoresist layer may be removed to expose the underlying chemisorption layer. The anchoring molecules may serve to bond with analyte molecules. By forming the anchoring molecules within only localized regions centered over respective pixels, spatial resolution of the imager when imaging the analyte molecules may be improved.

The foregoing is merely illustrative of the principles of this invention and various modifications can be made by those skilled in the art without departing from the scope and spirit of the invention.

What is claimed is:

1. An imager, comprising:
a substrate;
an array of pixels on the substrate;
a planar chemisorption layer over the array of pixels;
anchoring molecules that are bonded to the planar chemisorption layer in only localized regions each covering a respective pixel of the array of pixels; and
a photoresist layer that covers the planar chemisorption layer and is formed separately from the planar chemisorption layer, wherein openings in the photoresist layer define the localized regions.

2. The imager defined in claim 1 wherein the planar chemisorption layer comprises a polymer having active sites that chemically bond with the anchoring molecules.

3. The imager defined in claim 2 wherein the anchoring molecules are bonded only to the planar chemisorption layer.

4. The imager defined in claim 2 wherein the photoresist layer comprises a material that is chemically stable during alkaline conditions.

5. The imager defined in claim 4 wherein the photoresist layer comprises a polymer.

6. The imager defined in claim 5 wherein the active sites of the polymer comprise hydroxyl groups.

7. The imager defined in claim 5 wherein the planar chemisorption layer comprises a polymer having functional groups that bond with the anchoring molecules, wherein the functional groups are selected from the group consisting of: benzyl halides, alkyl halides, alkoxide, olefin, dienyl, thiol, amino, amido, and ester groups.

8. The imager defined in claim 1 further comprising:
a color filter layer interposed between the array of pixels and the planar chemisorption layer.

9. A method, comprising:
fabricating a pixel array on a substrate;
depositing a chemisorption layer having bonding sites;
after depositing the chemisorption layer, depositing a photoresist layer over the chemisorption layer, wherein depositing the photoresist layer comprises depositing a continuous photoresist layer across the entire pixel array;
after depositing the photoresist layer, patterning the photoresist layer using photolithography to remove portions of the photoresist layer, wherein remaining portions of the photoresist layer after patterning define localized openings in the photoresist layer over underlying pixels of the pixel array, wherein the openings do not include material of the photoresist layer, and wherein the localized openings in the photoresist layer expose the chemisorption layer; and
depositing anchoring molecules that bond with the bonding sites of the chemisorption layer in the localized openings of the photoresist layer.

10. The method defined in claim 9 wherein depositing the chemisorption layer having bonding sites comprises depositing a polymer layer having hydroxyl groups.

11. The method defined in claim 10 wherein depositing the anchoring molecules comprises depositing anchoring molecules having silicon oxide groups that chemically bond with the hydroxyl groups of the chemisorption layer.

12. The method defined in claim 9 wherein depositing the chemisorption layer comprises depositing a layer of silicon oxide having surface hydroxyl groups.

13. An imager, comprising:
   a substrate;
   an array of pixels on the substrate;
   a planar chemisorption layer over the array of pixels, wherein the planar chemisorption layer covers the entire array of pixels;
   anchoring molecules that are bonded to the planar chemisorption layer in only localized regions each covering a respective pixel of the array of pixels; and
   a photoresist layer that covers the planar chemisorption layer and is formed separately from the planar chemisorption layer, wherein the anchoring molecules are not bonded to the photoresist layer, wherein the photoresist layer has portions that define openings in which no material from the photoresist layer is formed, and wherein the openings define the localized regions.

14. The imager defined in claim 13 wherein the planar chemisorption layer comprises a polymer having active sites that chemically bond with the anchoring molecules.

\* \* \* \* \*